United States Patent [19]

Smith

[11] Patent Number: 4,947,323

[45] Date of Patent: Aug. 7, 1990

[54] METHOD AND APPARATUS FOR MEASURING SMALL SPATIAL DIMENSIONS OF AN OBJECT

[75] Inventor: Lewis M. Smith, Tullahoma, Tenn.

[73] Assignee: University of Tennessee Research Corporation, Knoxville, Tenn.

[21] Appl. No.: 270,490

[22] Filed: Nov. 8, 1988

Related U.S. Application Data

[63] Continuation of Ser. No. 866,233, May 22, 1986, abandoned.

[51] Int. Cl.$^5$ ............................................. G06F 15/42
[52] U.S. Cl. .................................. 364/413.13; 382/6; 382/8
[58] Field of Search ................ 364/414, 507; 358/111, 358/284, 166; 250/65, 156; 382/8, 54, 43, 724, 527, 6; 340/723-724, 789

[56] References Cited

U.S. PATENT DOCUMENTS

| | | | |
|---|---|---|---|
| 4,074,231 | 2/1978 | Yajima et al. | 340/146.3 |
| 4,164,788 | 8/1979 | Jain | 364/515 |
| 4,217,641 | 8/1982 | Naparstek | 364/414 |
| 4,298,895 | 11/1981 | Arai et al. | 358/284 |
| 4,298,944 | 11/1981 | Stoub et al. | 364/515 |
| 4,323,973 | 4/1982 | Greenfield | 364/515 |
| 4,335,427 | 6/1982 | Hunt | 364/414 |
| 4,446,521 | 5/1984 | Inouye | 364/414 |
| 4,499,598 | 2/1985 | Chittineni | 382/54 |
| 4,516,261 | 5/1985 | Harding | 382/6 |
| 4,517,607 | 5/1985 | Ohkouchi et al. | 358/284 |

Primary Examiner—Jerry Smith
Assistant Examiner—Gail O. Hayes
Attorney, Agent, or Firm—Luedeka, Hodges & Neely

[57] ABSTRACT

A method and apparatus are disclosed for measuring spatial dimensions of an object. The object is positioned between a radiation source and a radiation sensitive surface, such as between an X-ray unit and an X-ray film. The distance between the object and the X-ray unit is small relative to the distance between the object and the film. An the image of the object is produced on the film when radiation is emitted from the X-ray unit, and by virtue of the spacing of the object between the source and the film, the object is magnified, but is severely blurred. The image is then digitized and restored using two-dimensional deconvolution techniques to remove the blur, resulting in an enlarged, clear image. Edge-detection algorithms are then used to enable measurement of the spatial dimension. This permits accurate measurement of small internal dimensions of the object such as voids or cracks in bonded or welded components.

12 Claims, 5 Drawing Sheets

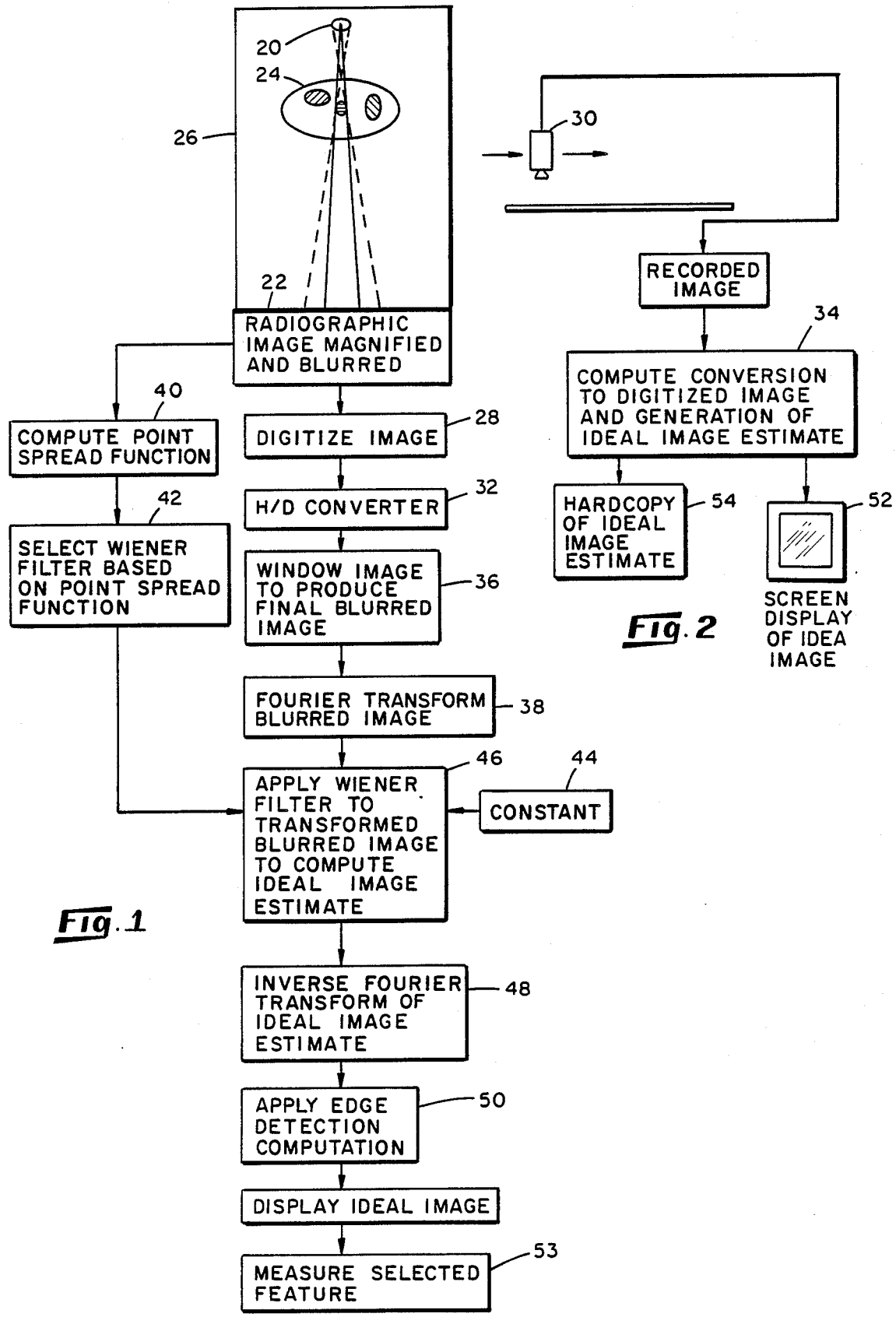

METHOD AND APPARATUS FOR MEASURING SMALL SPATIAL DIMENSIONS OF AN OBJECT

This application is a continuation of application Ser. No. 06/866,233, filed May 22, 1986 which is abandoned.

FIELD OF INVENTION

The present invention relates to methods and apparatus for making dimensional measurements of an object, and more particularly relates to a method and apparatus for measuring small spatial dimensions of an object from radiographic images thereof.

DESCRIPTION OF RELATED ART

Radiography using either X-ray or radioisotope sources has long been used as an effective method for non-obtrusive and non-destructive examinations of objects, especially for internal configurations. However, for precise measurements of small spatial dimensions, a fundamental problem exists. To minimize blurring of the image due to the penumbra effect, conventional radiography usually places the object as close as possible to the film and at a large distance from the source. In this way a nearly unitary magnification is obtained and the blurring of the image is minimized. The drawback of this technique is that artifacts produced on the film having small dimensions usually end up lost in the film and image noise, and are therefore unavailable for image analysis and/or measurement.

Methods have been developed for making accurate spatial measurements from X-ray radiographs. Descriptions of these methods can be found in L. M. Smith et al, "The Use of Image Models For Accurate Spatial Measurements from X-ray Radiographs." 1984 *Flash Radiography Symposium*. Columbus: The American Society For Nondestructive Testing, 1985 and in H. M. Pressley et al, "In Situ Burning Rate Determination Using Flash Radiography." Technical Report, Air Force Rocket Propulsion Laboratory. Edwards AFB, California, August, 1984. The approaches taken used mathematical models of radiographic image formation to calculate theoretical digital images which were then compared with the actual digitized radiograph. The theoretical image in best agreement with the actual radiograph yielded an estimate of the inner dimension of interest. The techniques, while effective for simple geometric objects and relatively large dimensions, become prohibitively difficult to apply to complicated objects. Thus, these approaches are of limited usefulness in most industrial applications.

There are many applications where it is desired to make precise measurements of small spatial dimensions of objects using nondestructive methods. A technique of this type would be valuable in industrial applications such as in obtaining measurements of blade clearance in turbine engines, small voids in bonded or welded components, cracks due to metal fatigue in pipe lines or other machinery subject to high stresses, and in quality control applications for small machined parts.

Accordingly, a need exists for a method and apparatus capable of measuring small spatial dimensions of objects, which dimensions have heretofore been lost in the film and image noise of conventional radiographic analysis of the images.

The present invention meets this need, among others, through provision of a method and apparatus for measuring small spatial dimensions of an object which uses a magnified blurred radiographic image of the object.

SUMMARY OF THE INVENTION

In accordance with a preferred form of the invention, a method is provided for measuring small spatial dimensions of an object and includes positioning the object between a radiation source and a radiation sensitive surface. Radiation is emitted from the radiation source so that a magnified blurred image of the object is produced on the radiation sensitive surface. The magnified blurred image is then digitized and the digitized image is filtered to produce a magnified clear image estimate. The edges of the selected feature in the magnified clear image estimate are detected, and the spatial dimension in the magnified clear image estimate is measured. The measurement is corrected based on the magnification factor of the image so that an actual measurement of the dimension is obtained. Preferably, the object is positioned adjacent the radiation source so that the distance between the radiation source and the object is small relative to the distance between the object and the radiation sensitive surface. A small spatial dimension within the object can thus be magnified to a larger dimension which can ultimately be measured and divided by the magnification factor to yield the absolute spatial measurement. Filtering the digitized magnified image to produce the magnified clear image estimate reveals the small dimension which, without the previous magnification, would have been lost in the film and image noise.

According to another aspect of the invention, the magnified blurred image is produced by making a radiograph of the object on a radiation sensitive film using a radiation source that emits radiation from a finite area, whereby the image blurring is a result of the penumbra effect due to the finite area of the radiation source from which the radiation is emitted. The degree to which the image is blurred is a blur function which is determined according to the area of the radiation source, the configuration of the finite area of the radiation source, the distance between the object and the radiation source, and the distance between the object and the film.

In accordance with a further aspect of the invention, the digitized magnified blurred image is filtered by computing the Fourier transform of the digitized blurred image, selecting a Wiener filter algorithm based on the blur function, applying the Wiener filter algorithm to the Fourier transform, and computing the inverse Fourier transform of the filtered image to produce the magnified clear image estimate. A constant may be introduced into the Wiener filter algorithm to account for random noise.

In accordance with still a further aspect of the invention, a preferred apparatus for use in the method described includes positioning means for positioning the object between a radiation source and a radiation sensitive surface and means for activating the radiation source to cause the source to emit radiation so that a magnified blurred image of the object is produced on the radiation sensitive surface. Means are provided for digitizing the magnified blurred image produced on the radiation sensitive surface, such means preferably including a video camera connected to the input of a computer where the image is stored. The computer is programmed to filter the digitized magnified blurred image to remove the blur and produce a magnified clear image estimate. The computer is further operable to detect the edges of the small spatial dimension in the magnified clear image estimate through an edge detection algorithm and measure the small spatial dimension. Additionally, the computer may be programmed to correct the measurement based on the magnification factor of the image so that an actual measurement of the dimension is obtained.

Other advantages and aspects of the present invention will be readily appreciated by those of ordinary skill in the art as the same becomes better understood by reference to the following detailed description of a preferred embodiment when considered in conjunction with the accompanying drawings in which:

BRIEF DESCRIPTION OF THE DRAWINGS

FIG. 1 is a block diagram illustrating steps in a method of measuring small spatial dimensions of an object according to a preferred form of the present invention;

FIG. 2 is a diagrammatical illustration showing features of a preferred apparatus for use in practicing the method of the present invention;

DESCRIPTION OF PREFERRED EMBODIMENT

Figure 3:
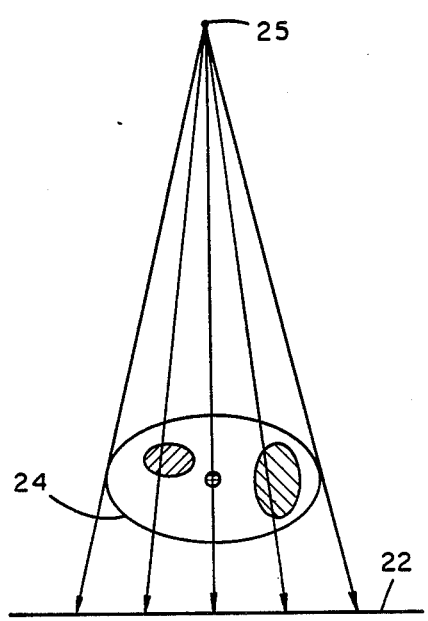
FIG. 3 is a diagrammatical illustration of an ideal point source emitting radiation in the direction of an object located between the point source and a radiation sensitive surface.

Referring now to the drawings in which like reference characters refer to the same or similar elements throughout the several views, steps in a preferred form of a method of measuring small spatial dimensions of an object according to the present invention are illustrated in FIG. 1. As used herein, the term "spatial" is used broadly to denote space and is intended to refer to features of an object such as internal voids, apertures or cracks as well as solid features thereof.

The present method provides intentional magnification of the object to bring out the small spatial dimension of interest which otherwise would be lost in the film and image noise. As will be more fully described, magnification produces blurring of the image, initially obscuring the small spatial dimension. However, through application of two-dimensional deconvolution techniques, as subsequently described, the blur is removed to produce an enlarged, clear image. Subsequent edge-detection algorithms are then used to measure of the now visible small spatial dimension.

The method employs the process of radiography which produces high-energy shadowgraphs by illuminating an object with a small intense source of X-rays or gamma rays. In the case of X-rays, the source is the anode of a two-terminal vacuum tube which is bombarded by electrons accelerated through a high voltage. Gamma ray sources are small pellets of radioactive material such as Cobalt 60, Cesium 137 or Iridium 192. Preferably, and as illustrated in the figures and subsequently described, an X-ray source 20 is used in combination with X-ray film 22. An object 24 to be examined is positioned between the source 20 and film 22.

Before describing the details of the invention, a brief background of the scientific principles involved will be provided to facilitate a better understanding thereof. For this purpose, initial reference is had to FIGS. 3 through 5.

Basically, as illustrated in FIG. 3, a radiographic image is formed when the incident radiation intensity propagating from a source 25 to the film 22 is attenuated as it passes through the object 24 in accordance with $$I(x,y) = I_0 \exp[-\Sigma \mu_i t_i] \tag{1}$$

where $I(x,y)$ is the intensity reaching the point $(x,y)$ in the film plane. $I_0$ is the unattenuated intensity, $\mu_i$ is the attenuation coefficient for the $i^{th}$ material comprising the object 24, and $t_i$ is the pathlength through the $i^{th}$ material along the line extending from the source 25 to the point $(x,y)$. The radiation intensity distribution $I(x,y)$ is recorded by the film 22, which after development yields an image termed a radiograph.

One important principle is illustrated in FIG. 3 wherein it is seen that because of the geometric configuration of the radiographic procedure, the physical extent of the object 24 is magnified in the image formation process. The magnification factor is given by $$M = z_s/(z_s - z_o) \quad (2)$$

where $z_s$ is the source-to-film distance and $z_o$ is the object-to-film distance. Theoretically, then, it is possible to enlarge the image of an object to any convenient size by moving the object closer to the source. A small dimension within the object can thus be magnified to a larger, tractable dimension which can then be measured and divided by the magnification factor N to yield the absolute spatial extent.

Figure 4:
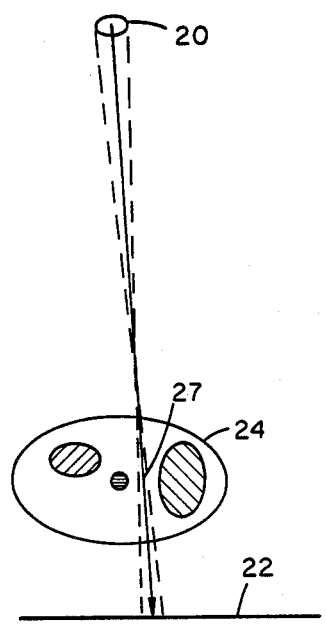
FIG. 4 is a diagrammatical illustration of the penumbra effect wherein a radiation source emits radiation from a finite area so that an infinite number of rays pass through a point in the object from the finite source area causing the image of the object at the point to be blurred over an area of the film.

Another physical effect must be considered, however. Radiation sources, while small, are not point sources as the source 25 shown in FIG. 3, but instead have a finite size such as the source 20 shown in FIG. 1 and reproduced in FIGS. 4 and 5. If a single point 27 within the object 24 is examined, as shown in FIG. 4, it is apparent that it is not a single ray that passes through the point 27 from the source 20 to the film 22. Instead, an infinite number of rays over the area of the source 20 pass through the point 27. The image at that one point in the object 24 is thus smeared, or spread out over the area of the film 22. In radiography, this process occurs for each point in or on the object 24 and the superposition of this process for all points within the object results in an overall blurring of the image, termed the penumbra effect. A thorough description of the penumbra effect can be found in G. A. Krusos, "Correction For X-Ray Source OpticalTransfer-Function Degradation of Radiologic Images by Optical Spatial Filtering," *Proceedings of the Society of Photo-Optical Instrumentation Engineers* (43): *Application of Optical Instrumentation in Medicine* Vol. II. Palos Verdes Estates, California; The Society of Photo-Optical Instrumentation Engineers, 1974, p.63–74 and in H. H. Barrett and W. Swindell, *Radiological Imaging*. New York: Academic Press, 1981. The amount of blurring is dependent upon the geometric configuration of the radiograph set-up. When the object is moved closer to the radiation source, that is, when the magnification is increased, the image is blurred more.

Because of the penumbra effect, conventional radiography usually places the object as close as possible to the film and at a large distance from the source. In this way a nearly unity magnification is obtained and the blurring of the image is minimized.

Figure 5:
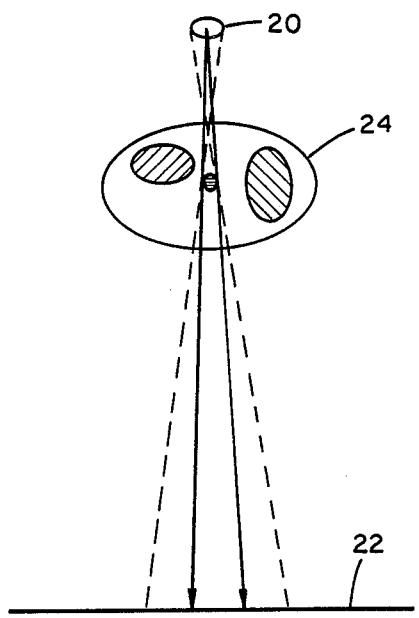
FIG. 5 is a diagrammatical illustration showing magnification of a small spatial dimension of the object and the resulting blurring of the image due to the penumbra effect as illustrated in FIG. 4.

In the method of the present invention to make measurements of small spatial dimensions of an object, however, the object 24 is placed close to the radiation source 20 and at a relatively large distance from the film 22 as shown in FIG. 5. Small details are therefore enlarged in a known fashion by the magnification principle and the image is blurred by the penumbra effect. The initial image obtained is usually so badly degraded by blurring that the small spatial dimension of interest is unrecognizable upon visual inspection of the image.

To process the image to a usable form, it is necessary to "un-do" the blurring due to the penumbra effect. That is, the image must be transformed to the ideal magnified image of the object 24 which would result if the object 24 where radiographed using an ideal point source 25 as shown in FIG. 3, and as imposed on the source 20 shown in FIG. 5. Image restoration is therefore a necessary step of the method in order to extract the desired information.

Image restoration refers to the process of estimating an ideal image from a degraded or ill-defined image produced on the film 22 in the image production step 26 shown in FIG. 1. In the present method, it is desired to remove the blurring caused by the penumbra effect from the radiograph to produce the ideal magnified image.

Linear systems theory, from the field of communications, has proven useful in mathematically describing the degradation of a radiographic image due to the finite size of the radiation source. See, e.g., H. H. Barrett and W. Swindell. *Radiological Imaging*. New York: Academic Press, 1981 and G. A. Krusos, "Correction For X-Ray Source Optical-Transfer-Function Degradation of Radiologic Images by Optical Spatial Filtering," *Proceedings of the Society of Photo-Optical Instrumentation Engineers* (43): *Application of Optical Instrumentation in Medicine* Vol. II. Palos Verdes Estates, Calif.: The Society of Photo-Optical Instrumentation Engineers, 1974, p.63–74. This approach employs the concept of a "black box" with the ideal image as an input two-dimensional function and the blurred image as the output function. If the system model is assumed to be linear and sift-invariant, as an impulse response to the two-dimensional delta function given by some function $h(X,Y)$ then the input and output are related by the convolution integral:

$$g(x,y) = \int_{-\infty}^{\infty} \int_{-\infty}^{\infty} f(x - \eta, y - \zeta) h(\eta,\zeta) d\eta d\zeta \quad (3)$$

where $f(x,y)$ is the ideal image input function and $g(x,y)$ is the blurred image output function.

Figure 6:
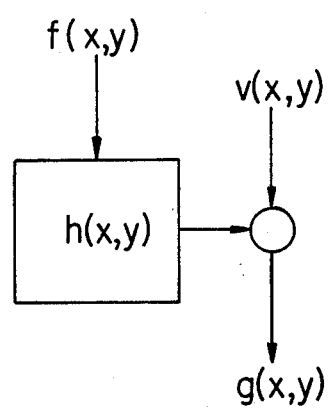
FIG. 6 is a diagrammatical illustration of a linear system model of radiographic image degradation.

Random noise also affects the degradation of the radiographic image and may arise from film anomalies, quantum mottle or numerous other sources and is usually assumed additive. Thus, the final degraded image is mathematically described by $$g(x,y) = \int_{-\infty}^{\infty} \int_{-\infty}^{\infty} f(x - \eta, y - \zeta) h(\eta,\zeta) d\eta d\zeta + v(x,y) \quad (4)$$

where $v(x,y)$ is a random signal. A block diagram for this process is shown in FIG. 6.

Image processing is most conveniently carried out by digitizing the continuous radiograph produced at step 26 to convert it to a two-dimensional array of pixels, each of which is assigned a numerical value equal to $g(x,y)$ in a small region about $(x,y)$. The digitized image is preferably produced through an optical scanning technique in step 28 following production of the radiographic image, and is represented diagrammatically in FIG. 2 where an optical scanner 30, which may be a video camera, is employed for recording the image and inputting the image to a computer 34 where the image is digitized as described. In this way, the equation for the degraded image can be approximated by its discrete counterpart:

$$g(m,n) = \sum_{k=0}^{m-1} \sum_{l=0}^{m-1} f(m-k, n-1)h(k,l) + v(m,n) \quad (5)$$

where the integer variables m and n refer to the digitized pixel locations in the x-y plane, and where k and 1 correspond to the dummy variables $\eta$ and $\zeta$ discretized to approximate the consolution integral by summation. Equation (5) therefore serves as the mathematical model for the degradation of the radiographic image which is to be restored.

In order to calculate an estimate for an ideal pixel array, f(m,n), a parametric Wiener filter is used. See R.C. Gonzalez and P. Wintz. *Digital Image Processing*. Ontario: Addison-Wesley, 1977 and H.C. Andrews and B.R. Hunt. *Digital Image Restoration*. Englewood Cliffs, N. J. Prectice-Hall 1977 for descriptions of Wiener filter techniques similar to that used in the present method. Taking the discrete Fourier transform of equation (5) yields the linear multiplicative relation $$G(w_x, w_y) = F(w_x, w_y)H(w_x, w_y) + V(w_x, w_y) \quad (6)$$

where upper case letters represent the Fourier transforms of the functions noted by the corresponding lower case letters. Each transform is a function of the spatial frequencies $w_x$ and $w_y$. The frequency-domain estimate of $F(w_x, w_y)$, denoted by $\hat{F}(w_x, w_y)$, is found by applying a parametric approximation of the Wiener filter to the Fourier transform of the degraded image, $G(w_x, w_y)$. Thus, the ideal image estimate is given by $$\hat{F}(w_x, w_y) = H^*(w_x, w_y)G(w_x, w_y)[|H(w_x, w_y)|^2 + P]^{-1} \quad (7)$$

where P is an empirically determined constant parameter. The inverse Fourier transform of $\hat{F}(w_x, w_y)$ yields the digital ideal image estimate, $\hat{f}(m,n)$.

Having outlined the basic theory of image restoration, it should be noted that before the parametric Wiener filter can be applied to a digitized radiograph, certain practical considerations must be taken into account. The recording of the image on the film 22 and the sampling of the image in the digitization process both present special problems when digital signal filtering techniques are applied. Also, the Wiener filter restoration scheme requires knowledge of the blur function, h(m,n), whole functional form must be determined prior to application.

As mentioned above, image restoration is based upon linear systems theory The response of photographic film to incident radiation, however, is highly non-linear. Thus, the first step in restoring a digitized radiograph is to invent the effects of the film 22. This step is indicated at 32 in FIG. 1 and is referred to as the H/D converter step 32 which converts the film transmittance value at each pixel to the corresponding radiation intensity exposing the film adjacent the pixel location in the digitized image.

Film effect inversion requires knowledge of the Hurter-Driffeld, or H-D curve for the particular film being used. The H-D curve plots the negative logarithm of the film transmittance verses the logarithm of exposure, and usually takes a functional form. If the H-D curve is not available from the manufacturer, other well known empirical method exist for determining the film response.

Another factor which mu t be accounted for in the processing of the digitized image arises from the fact that digital signal frequency-domain processing assumes periodicity in both the vertical and horizontal directions of a finite size array. When an image is digitized, it is necessarily truncated to a finite size. The different values of pixels along the top and bottom and the left and right borders of the image can thus give rise to sharp discontinuities when the image is considered periodic in two dimensions. The application of the restoration scheme will drastically enhance the high spatial frequencies making up these discontinuities resulting in a "restored" image which is obliterated by these enhanced high frequency components.

To avoid the adverse affects arising from border discontinuities, the image must be "windowed," or gradually tapered to zero around the borders. This step in the method is indicated at step 36 of FIG. 1 and may be performed following the HD converter step 32 as indicated.

A useful window function for an M by N pixel digital image has been found to be a modified Hamming window given by $$w(m,n) = 0.25(1 + \cos[\pi(2m-M-1)/M])(1 + \cos[\pi(2n-N-1)/N]) \quad (8)$$

Before applying the Wiener filter, the degraded image g(m,n) is multiplied by w(m,n). After application of the filter, it is often useful to multiply the restored image $\hat{f}(m,n)$ by $W^{-1}(m,n)$ to enhance the outer portions.

Following the windowing of step 36, the Fourier transform is taken of the corrected digitized image and is indicated at step 38.

In order to apply the parametric Wiener filter of equation (7) to the transformed degraded image g(m,n) the blur function impulse response h(x,y) must be obtained. Sampling this function at the appropriate pixel spacing will yield h(m,n). In accordance with the discussion above, the blurring of a single point, i.e., a two-dimensional delta function, is a geometric scaling of the radiation source due to the rays passing through that point. The analogy of a pinhole camera may aid in conceptualizing this analysis. With the satisfaction of some approximations, the blur function or the point spread function, as it is sometimes called, is given by $$h(x,y) = s(-x[z_s - z_o]/z_o, -y[z_s - z_o]/z_o) \quad (9)$$

where again $z_s$ is the source-to-film distance, $z_o$ is the object-to-film distance and s(x,y) is a function describing the shape and extent of the radiation source 20.

With prior knowledge of the radiation source 20, the blur function h(m,n) can be calculated analytically from the above equation and the calculation thereof is indicated at step 40 in FIG. 1. The blur function may also be determined expirically by exposing a sheet of attenuating material such as lead with a pinhole in it in the same radiographic configuration as the examined object.

Once the blur function is obtained, a suitable Wiener after is selected based on the point spread function for use in equation (7) above, this selection being indicated in FIG. 1 as step 42. As described in equation (7), the Wiener filter and a constant shown at 44 are then used in combination with the transformed, digitized blurred image to obtain an ideal image estimate, this step in the method being indicated at step 46 in FIG. 1. The inverse Fourier transform of the ideal image estimate is then taken at step 48, followed by application of an edge detection algorithm at step 50.

As shown in FIG. 2, the ideal image estimate may be displayed on a screen 52 and/or recorded on graph paper or the like to obtain a hand copy as at 54. The thus obtained ideal image estimate, including the results of the edge-detection overlayed thereon, is then available for obtaining a measurement of the small spatial dimension of interest, indicated at step 53 in FIG. 1. The measurement obtained is scaled by the appropriate magnification factor given by equation (2) to arrive at the actual measurement of the spatial dimension.

Figure 7:
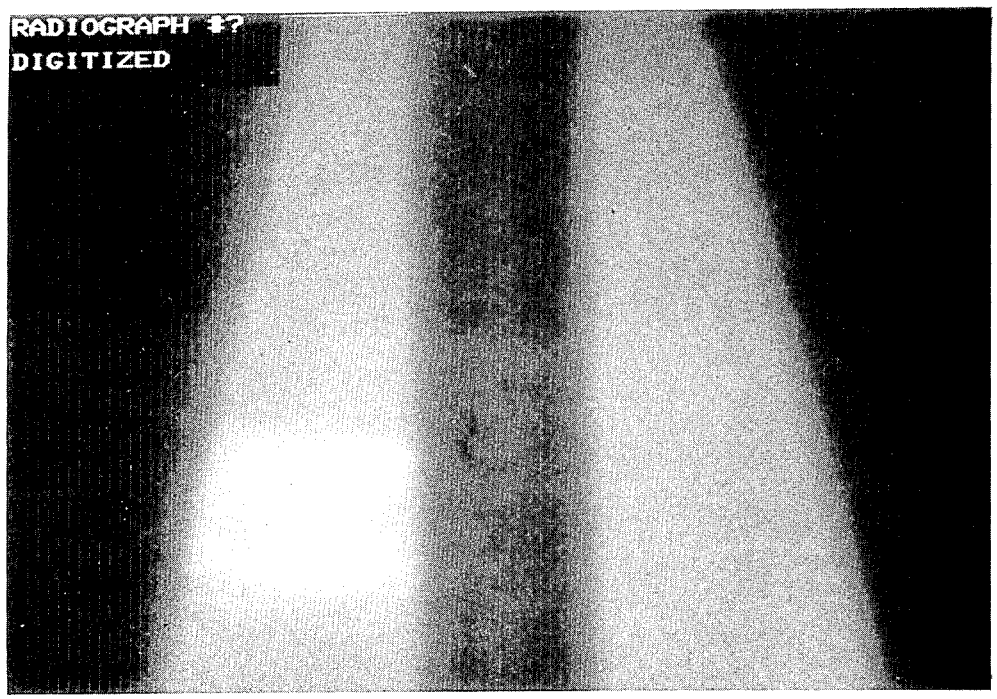
FIG. 7 is a photograph of a digitized blurred image.

The method and apparatus of the present invention was applied in obtaining the measurement of a gap between two precision metal parts. The gap was set at 0.055 inches. The source 20 was a 450 kVp industrial X-ray unit located 80 inches from the film 22. The parts were positioned with the stated gap separation between the source 20 and the film 22 at a distance of 60 inches from the film 22. This, the magnification factor M equaled 4.0. the radiograph obtained was digitized for analysis and is shown in the photograph of FIG. 7.

Figure 8:
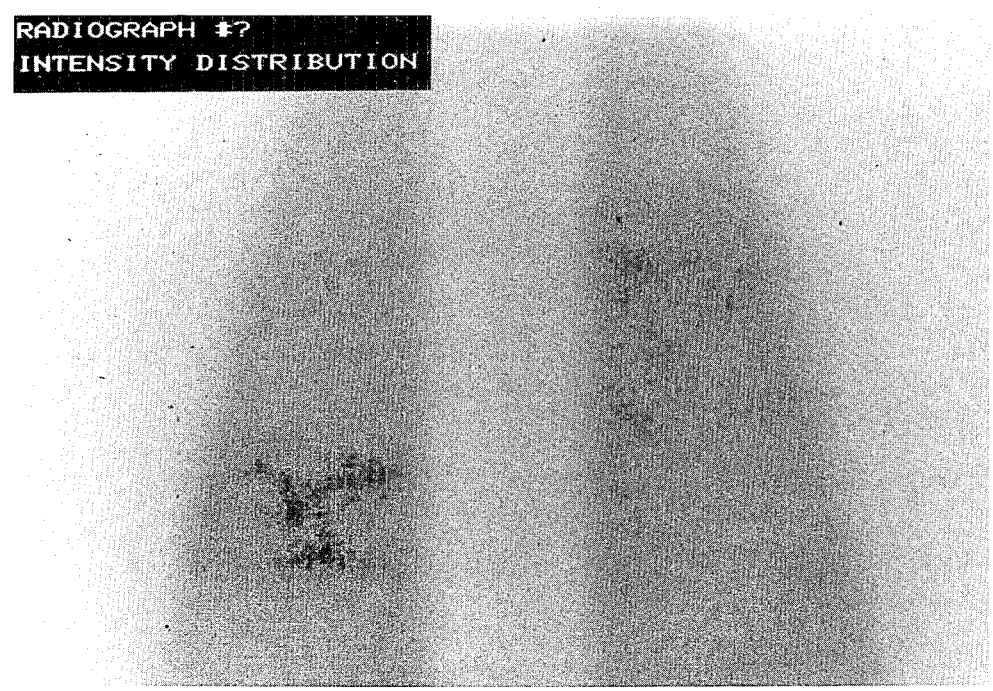
FIG. 8 is a photograph of the image of FIG. 7 wherein the film transmittance is converted to an intensity distribution.

The non-linear effects of recording on photographic film were determined by using a series of copper strips placed on the film cassettes at the time of exposure. The strips were stacked on each other in an overlapping step fashion so as to present different known thicknesses through which the incident radiation must pass in order to expose the film. By using the exponential attenuation principle of equation (1), the relative intensity reaching the film through each step thickness could be calculated using the attenuation coefficient for copper. The film transmittance under each step was found from pixel values on the digitized radiographs. Taking the logarithm of each corresponding intensity/transmittance pair of values allowed the plotting of a number of discrete points on the H-D curve. A suitable continuous function was then curve fit through the points to give an ad hoc H-D curve from the film. In this way, the film transmittance for each pixel could be directly and uniquely related to the incident radiation intensity producing it. FIG. 8 shows the digitized radiograph of FIG. 7 converted to intensity distributions using the ad hoc H-D curve. Note that, like a shadow, light corresponds to high intensity and dark to low intensity.

Figure 9:
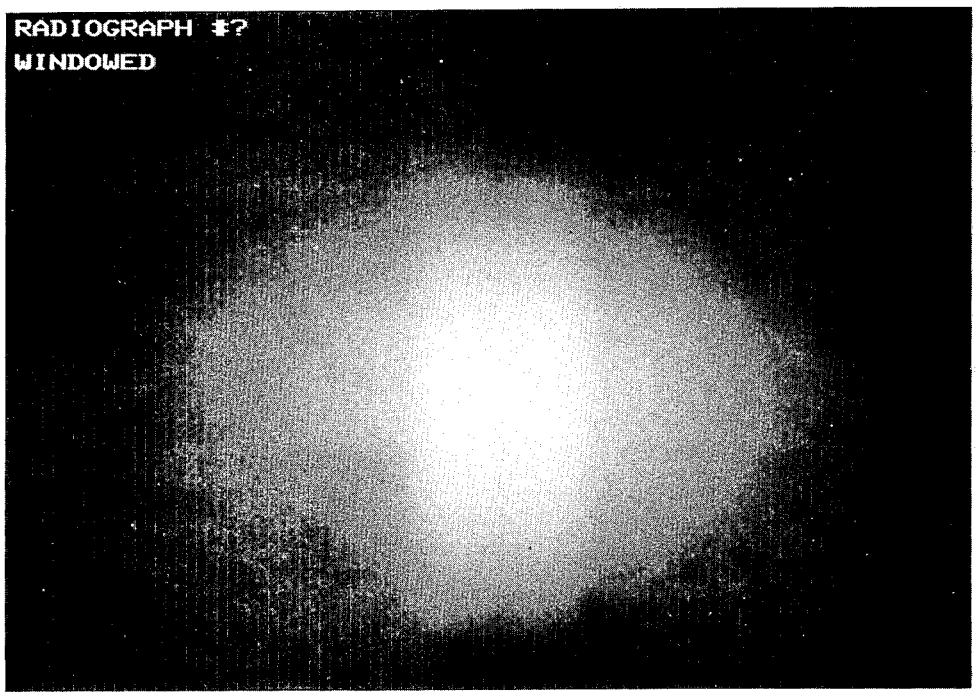
FIG. 9 is a photograph of the image of FIG. 8 windowed to avoid the adverse affects arising from border discontinuities in the recorded image.
Figure 10:
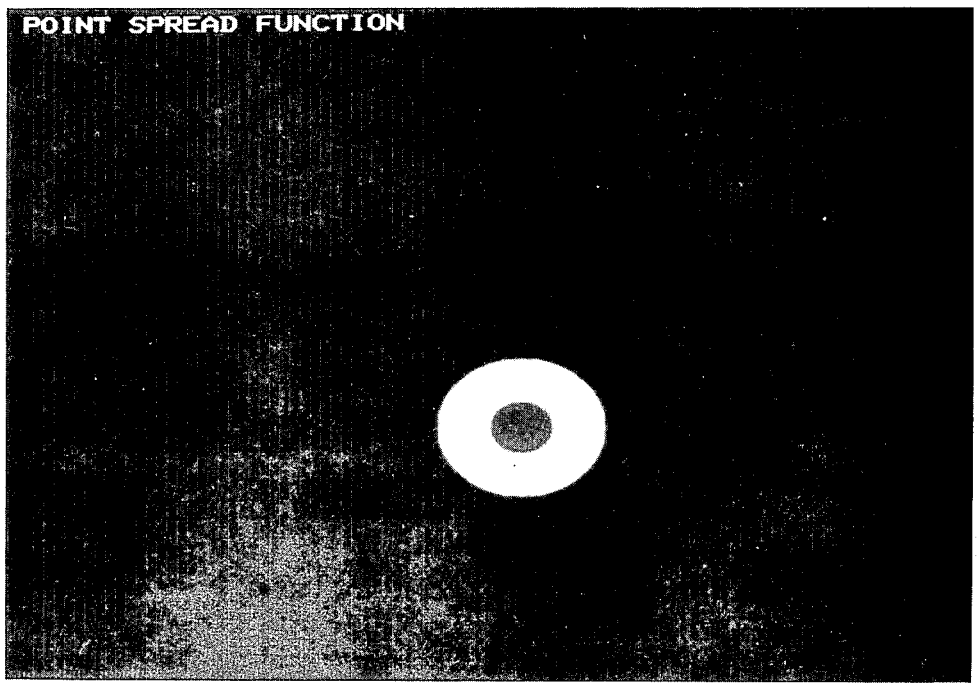
FIG. 10 is a photograph of a blur function calculated from knowledge of the radiation source and the spacing of the object between the source and the film.

FIG. 9 shows the image of FIG. 8 windowed through application of equation (8) for application of the restoration algorithm. The blur function h(x,y) was calculated from knowledge of the X-ray unit as described. In this case, the angle was sharply pointed tungsten target surrounded by a circular cathode. The resulting source function s(x,y) was an annulus which was scaled by the appropriate geometric factors according to equation (9) to yield h(x,y) and the digital scaled blur function h(m,n) is shown in the photograph of FIG. 10.

Figure 11:
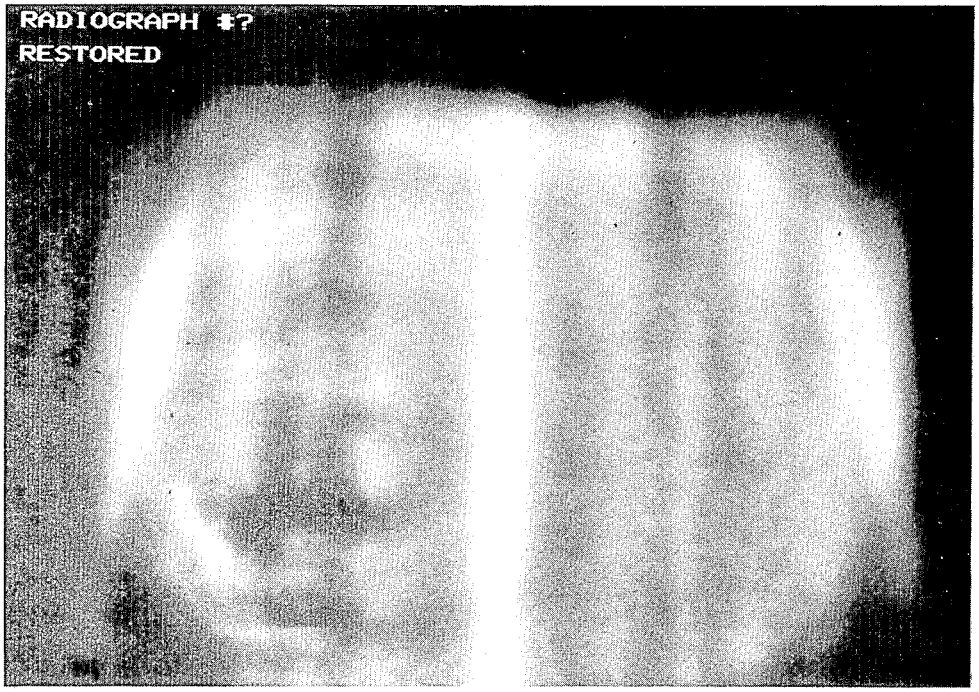
FIG. 11 is a photograph of a restored image produced through application of a Wiener filter algorithm to the image shown in FIG. 9 with the Wiener filter algorithm being selected on the basis of the blur function illustrated in FIG. 10.
Figure 12:
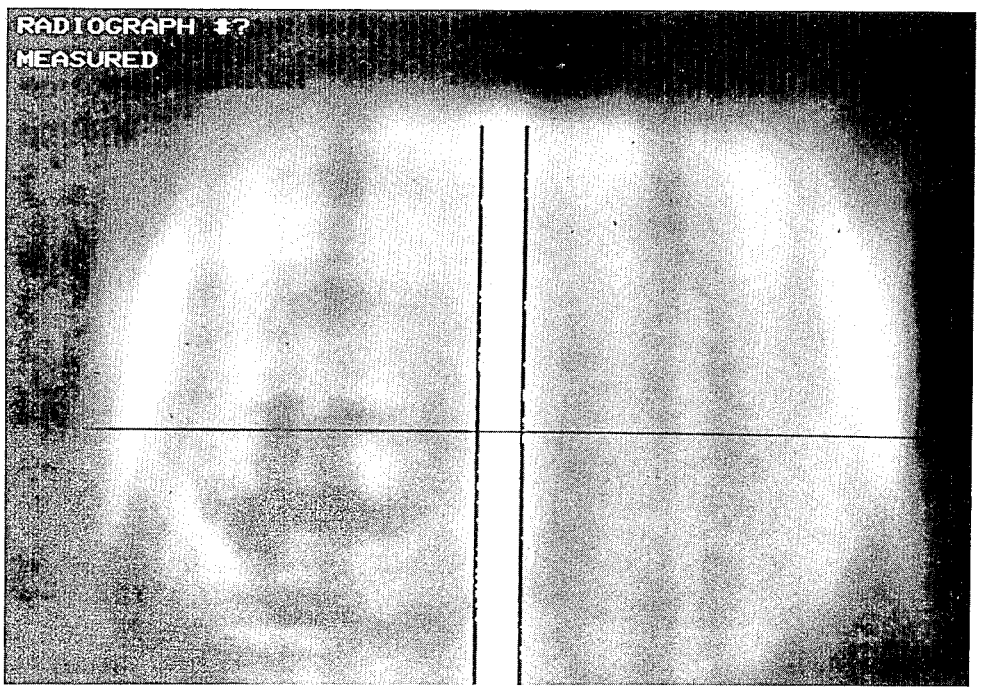
FIG. 12 is a photograph of the restored image of FIG. 11 showing application of a standard edge detection algorithm to detect and measure the spatial dimension of the object.

The application of a parametric Wiener filter using array processing hardware in the computer 34 of FIG. 2 yielded the restored images shown in the photograph of FIG. 11. The white strip running down the restored image corresponds to the gap between the parts magnified by the radiographic procedure. The sharpened edges allowed the use of a standard edge detection algorithm as described to measure the width of the stripe in the image. The results of the edge detection are overlayed in graphics on the restored image shown in FIG. 12. The dimension of the gap was measured and the appropriate magnification factor M was used to obtain the final separation value.

The measurement yielded a separation value of 0.0058 inches for the radiograph. This value is compared with the actual gap setting of 0.055 inches at which the metal parts were positioned prior to radiographic examination. The absolute spatial error was thus +0.003 inches for the radiograph.

Having thus fully described a preferred form of the method and apparatus of the present invention, it is seen that the invention is capable of making precise measurements of spatial dimensions of objects. Heretofore, magnification of objects to obtain measurements of small spatial dimensions has not been thought practical since the magnified images were severely blurred and degraded due to the penumbra effect and noise factors. However, through the image restoration techniques of the present invention the blurred and degraded magnified image provides a basis for accurately estimating the clear image from which the spatial dimensions can be obtained. The invention is particularly useful in industrial applications for detecting the existence and dimensions of cracks, voids, and the like in machined or welded parts including pipes, etc., where the existence and nature of such features are of critical importance.

While a particular embodiment of the present invention has been shown and described, it will be understood that the invention is capable of numerous rearrangements, modifications and substitutions of steps and parts without departing from the scope of the invention as set forth in the claims below.

What is claimed is:

1. A method of measuring a small spatial dimension of an object, said small spatial dimension being too small to enable production of an image of the dimension having visually meaningful size information by a conventional radiographic technique in which the object containing the dimension is placed as near as possible to a radiation sensitive surface, the method comprising:

placing the object between a radiation source and the radiation sensitive surface so that radiation emitted from the source produces a radiographic image of the object on the radiation sensitive surface;

positioning the object in a spaced relationship with the radiation sensitive surface so that a blurred magnified radiographic image of the object and the small spatial dimension is produced on the radiation sensitive surface when radiation is emitted from the radiation source, the spacing being sufficient to blur and substantially obscure the image of the small spatial dimension to the extent that the image of the small spatial dimension is substantially unmeasurable by direct visual measurement;

emitting radiation from the radiation source so that the blurred magnified image of the object including an image of the substantially obscured and unmeasurable small spatial dimension is produced on the radiation sensitive surface;

digitizing the blurred magnified image to produce a digitized image;

filtering the digitized image based on a blur function which is determined according to the source-to-film distance, the object-to-film distance, and the configuration of the radiation source to remove the blur from the digitized image and produce a magnified clear image estimate;

detecting an outline of the small spatial dimension in the magnified clear image estimate; and measuring the small spatial dimension in the magnified clear image estimate from the detected outline.

2. The method of claim 1, further comprising correcting the measurement of the small spatial dimension based on the magnification of the image, whereby an actual measurement of the dimension is obtained.

3. The method of claim 1, wherein the object is positioned adjacent to the radiation source so that the distance between the radiation source and the object is small relative to the distance between the object and the radiation sensitive surface.

4. The method of claim 1, wherein the filtering of the digitized image comprises:

determining the Fourier transform of the digitized image;

selecting a Wiener filter algorithm based on the radiation source and the position of the object relative to the radiation source and the radiation sensitive surface;

applying the Wiener filter algorithm to the Fourier transform of the digitized image to produce a filtered image; and determining the inverse Fourier transform of the filtered image to produce the magnified clear image estimate.

5. The method of claim 1, further comprising:

determining the radiation response curve of the radiation sensitive surface; and correcting the digitized image using the response curve to produce a digitized intensity distribution image that corresponds to the radiation intensity incident on the radiation sensitive surface.

6. The method of claim 1, further comprising gradually tapering the digitized magnified blurred image to zero around its borders prior to filtering the image to produce a windowed image for filtering.

7. An apparatus for measuring a small spatial dimension of an object, said small spatial dimension being too small to enable production of an image of the dimension having visually meaningful size information by a conventional radiographic technique in which the object containing the dimension is placed as near as possible to a radiation sensitive surface, the method comprising:

a radiation source;

a radiation sensitive surface;

placement means for placing the object between the radiation source and the radiation sensitive surface so that radiation emitted from the source produces a radiographic image of the object on the radiation sensitive surface;

positioning means for positioning the object in a spaced relationship with the radiation sensitive surface so that a blurred magnified radiographic image of the object and the small spatial dimension is produced on the radiation sensitive surface when radiation is emitted from the radiation source, the spacing being sufficient to blur and substantially obscure the image of the small spatial dimension to the extent that the image of the small spatial dimension is substantially unmeasurable by direct visual measurement;

activation means for activating the radiation source so that the source emits radiation and the blurred magnified image of the object including an image of the substantially obscured and unmeasurable small spatial dimension is produced on the radiation sensitive surface;

digitizing means for digitizing the blurred magnified image to produce a digitized image;

filtering means for filtering the digitized image based on a blur function which is determined according to the source-to-film distance, the object-to-film distance, and the configuration of the radiation source to remove the blur from the digitized image and produce a magnified clear image estimate;

detection means for detecting an outline of the small spatial dimension in the magnified clear image estimate; and means for measuring the small spatial dimension in the magnified clear image estimate from the detected outline.

8. The apparatus of claim 7, further comprising means for correcting the measurement of the small spatial dimension based on the magnification of the image, whereby the actual measurement of the dimension is obtained.

9. The apparatus of claim 7, wherein said positioning means is operable to position the object adjacent to the radiation source so that the distance between the radiation source and the object is small relative to the distance between the object and the radiation sensitive surface.

10. The apparatus of claim 7, wherein said filtering means comprises:

means for determining the Fourier transform of a digitized image;

a Wiener filter, said Wiener filter being selected based on said radiation source and the position of the object relative to said radiation source and said radiation sensitive surface;

means for applying said Wiener filter to the Fourier transform of the digitized image to produce a filtered image; and means for determining the inverse Fourier transform of the filtered image to produce the magnified clear image estimate.

11. The apparatus of claim 7, further comprising:

means for determining the radiation response curve of the radiation sensitive surface; and means for correcting the digitized image using the response curve to produce a digitized intensity distribution image that corresponds to the radiation intensity incident on the radiation sensitive surface.

12. The apparatus of claim 7, further comprising windowing means for producing a windowed image for filtering, said windowing means operable to gradually taper the digitized magnified blurred image to zero around its borders prior to filtering the image.

* * * * *

UNITED STATES PATENT AND TRADEMARK OFFICE
CERTIFICATE OF CORRECTION

PATENT NO. : 4,947,323
DATED : August 7, 1990
INVENTOR(S) : Lewis M. Smith

It is certified that error appears in the above-identified patent and that said Letters Patent is hereby corrected as shown below:

Column 5, line 7, "TheoreticallY" should be -- Theoretically --.

Column 5, line 12, "N" should be -- M --.

Column 6, line 31, "sift" should be -- shift --.

Column 7, line 17, "Prectice" should be -- Prentice --.

Column 7, line 34, "F" should be -- $\hat{F}$ --.

Column 7, line 37, "F" should be -- $\hat{F}$ --.

Column 7, line 38, "f" should be -- $\hat{f}$ --.

Column 7, line 52, after theory insert -- . --.

Column 7, line 56, "invent" should be -- invert --.

UNITED STATES PATENT AND TRADEMARK OFFICE
CERTIFICATE OF CORRECTION

PATENT NO. : 4,947,323

DATED : August 7, 1990

INVENTOR(S) : Lewis M. Smith

It is certified that error appears in the above-identified patent and that said Letters Patent is hereby corrected as shown below:

Column 8, line 3, "mu t" should be -- must --.

Column 8, line 23, "H D" should be -- H/D --.

Column 8, line 61, "expirically" should be -- empircally --.

Column 8, line 66, "after" should be -- filter --.

Column 9, line 11, "hand" should be -- hard --.

Column 9, line 17, after factor insert -- M --.

Column 9, line 27, delete "This" and insert -- Thus --.

Column 9, line 60, "angle" should be -- anode --.

Signed and Sealed this

Tenth Day of March, 1992

*Attest:*

HARRY F. MANBECK, JR.

*Attesting Officer*  *Commissioner of Patents and Trademarks*